(12) United States Patent
Zwart

(10) Patent No.: US 7,463,813 B2
(45) Date of Patent: Dec. 9, 2008

(54) MEDICAL EXAMINATION SYSTEM

(75) Inventor: Paul Zwart, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/531,604

(22) PCT Filed: Sep. 19, 2003

(86) PCT No.: PCT/IB03/04222

§ 371 (c)(1),
(2), (4) Date: Apr. 14, 2005

(87) PCT Pub. No.: WO2004/036527

PCT Pub. Date: Apr. 29, 2004

(65) Prior Publication Data

US 2006/0165371 A1    Jul. 27, 2006

(30) Foreign Application Priority Data

Oct. 18, 2002    (EP) .................................. 02079334

(51) Int. Cl.
*G02B 6/00*    (2006.01)
(52) U.S. Cl. ............................. 385/147; 235/375; 705/2
(58) Field of Classification Search .................. 385/147
See application file for complete search history.

(56) References Cited

U.S. PATENT DOCUMENTS

| 5,996,889 A * | 12/1999 | Fuchs et al. ................. 235/375 |
| 6,621,890 B1 | 9/2003 | Rondeux |
| 2002/0081080 A1* | 6/2002 | Balle-Petersen et al. ...... 385/93 |
| 2003/0052788 A1* | 3/2003 | Kwong-Tai Chung .... 340/573.1 |
| 2006/0053036 A1* | 3/2006 | Coffman et al. ................. 705/2 |

FOREIGN PATENT DOCUMENTS

| WO | WO9215977 | 9/1992 |
| WO | WO9406106 | 3/1994 |
| WO | WO0030416 | 5/2000 |

\* cited by examiner

*Primary Examiner*—Sarah Song

(57) ABSTRACT

A medical examination system includes a medical examination device and a control device to operate the medical examination device. The control device transmits signals including control signals accompanied by an identification code. The examination device is provided with a verifier to verify the identification code and is arranged to accept the corresponding control signals when the identification code is correct, and to reject the corresponding control signals when the identification code is not correct. The examination system further automatically communicates the identification code between the control device and the examination device.

17 Claims, 4 Drawing Sheets

MEDICAL EXAMINATION SYSTEM

Figure 1:
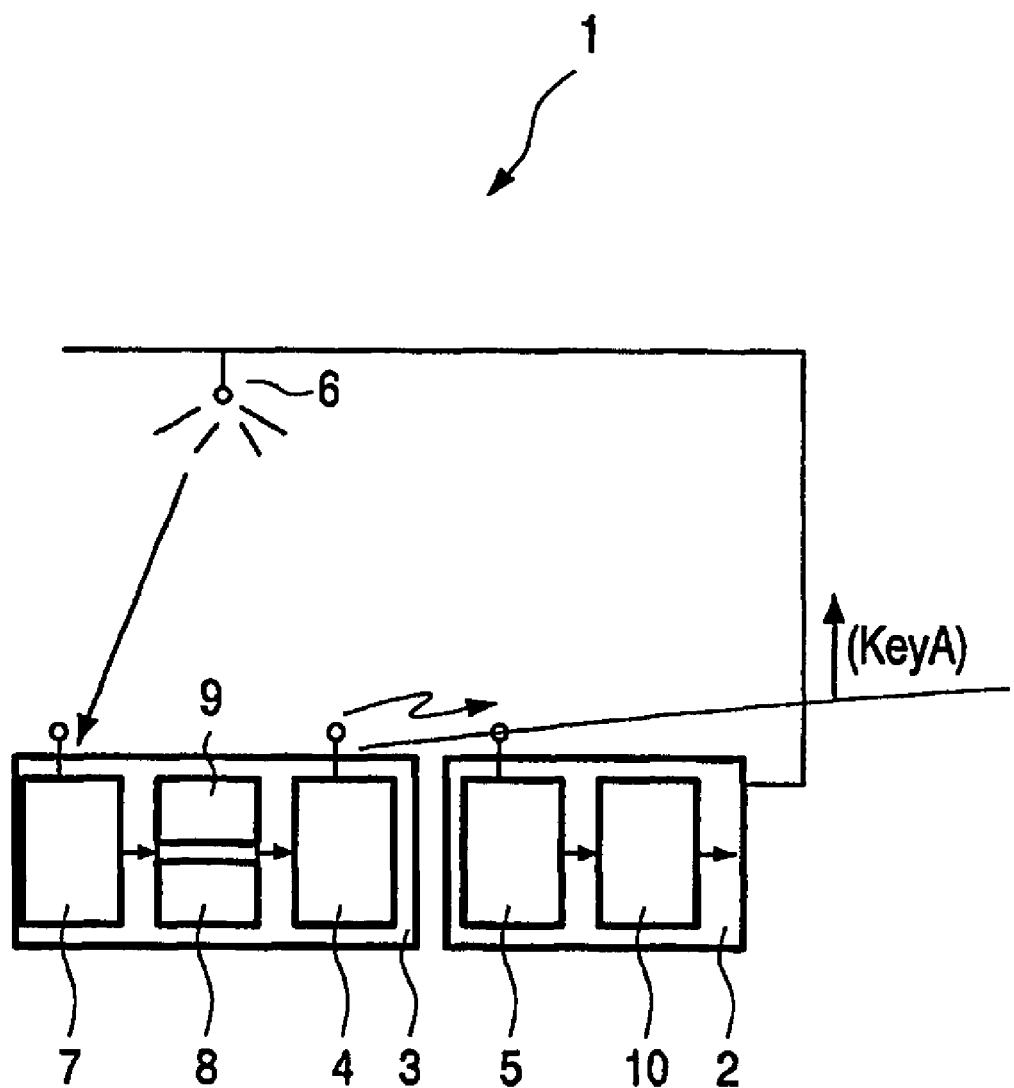

The present invention relates to a medical examination system comprising a medical examination device and a control device to operate the medical examination device, wherein the control device transmits signals comprising control signals accompanied by an identification code and wherein the examination device is provided with means to verify the identification code and is arranged to accept the corresponding control signals when the identification code is correct and to reject the corresponding control signals when the identification code is not correct.

Such a medical examination system is known from the international patent application WO 00/30416. In the known system the medical examination device it is intended to operate has to be made known to the control device first. This needs to be performed by a manual coupling action, for instance by placing the control device in front of the medical examination device or by establishing a cable connection between said devices. During this coupling the identification code necessary for wireless operation is transmitted.

The manual character of the necessary coupling act introduces a potential danger, since it can easily be forgotten. When a wireless control device is removed from an examination room it will still operate the medical examination device in that examination room. When the control device is brought into another examination room it will operate the medical examination device in the previous examination room until the necessary coupling to the medical examination device in the same examination room is established. Evidently this may lead to potentially very dangerous situations. Probably the forgotten coupling act will only be discovered while one tries in vain to operate the medical examination device in the same examination room during which one is not knowingly operating the medical examination device in the previous examination room. In another situation when the control device is kept in storage, for repair or recharging, a potentially dangerous situation occurs each time the control device is inadvertently activated.

It is an object of the invention to provide a device of the type as described above that solves this problem.

The medical examination device according to the invention is therefore characterised in that the examination system further comprises means for automatically communicating the identification code between the control device and the examination device.

In a first preferred embodiment of the device according to the invention the communication means are arranged to receive the identification code from the medical examination device for transmittance to the control device.

According to a further preferred embodiment the communication means are arranged for periodically transmitting the identification code and the control device is provided with memory means for temporal storage of the identification code. Advantageously the control device automatically forgets the identification code when it is out of reach of the communication means.

Preferably the communication means comprise Infra Red transmitter means and the control device is provided with Infra Red receiver means. Infra Red communication means have a limited reach thus allowing the identification code to be transmitted only in a confined area, such as the examination room in which the examination device is located.

In a second preferred embodiment of the device according to the invention the communication means are arranged to receive the identification code from the control device for transmittance to the examination device.

In a practical embodiment the communication means comprise interrogation means for periodically retrieving the identification code from the control device.

Preferably the interrogation means comprise an RFID reader and the control device is provided with an RFID tag. RFID means have a limited reach thus allowing the identification code to be transmitted only in a confined area, such as the examination room in which the examination device is located.

In yet a further preferred embodiment the control device is provided with a radio frequent transmitter and the examination device is provided with a radio frequent receiver. The use of radio frequent (RF) equipment allows the signals to travel undisturbed thus assuring a high degree of reliability of the control over the system.

In an elegant embodiment the identification code comprises a room identification code identifying the room in which the examination device is located.

In a practical embodiment the examination device comprises an X-ray device. As an X-ray device is potentially dangerous for human health and needs to be operated only under professional supervision the invention is very useful in combination with an X-ray system. In a further practical embodiment the control device is an X-ray foot switch.

The invention also refers to a method for automatically communicating an identification code between a control device and a medical examination device in a medical examination system according to a first embodiment of the invention comprising the steps of: receiving the identification code from the medical examination device by the communication means; transmitting the identification code periodically to the control device by the communication means; and temporally storing the identification code in the memory means of the control device.

The invention also refers to a method for automatically communicating an identification code between a control device and a medical examination device in a medical examination system according to a first embodiment of the invention, comprising the steps of: periodically interrogating the control device by the communication means for retrieving the identification code; and transmitting the identification code to the examination device by the communication means.

Figure 2:
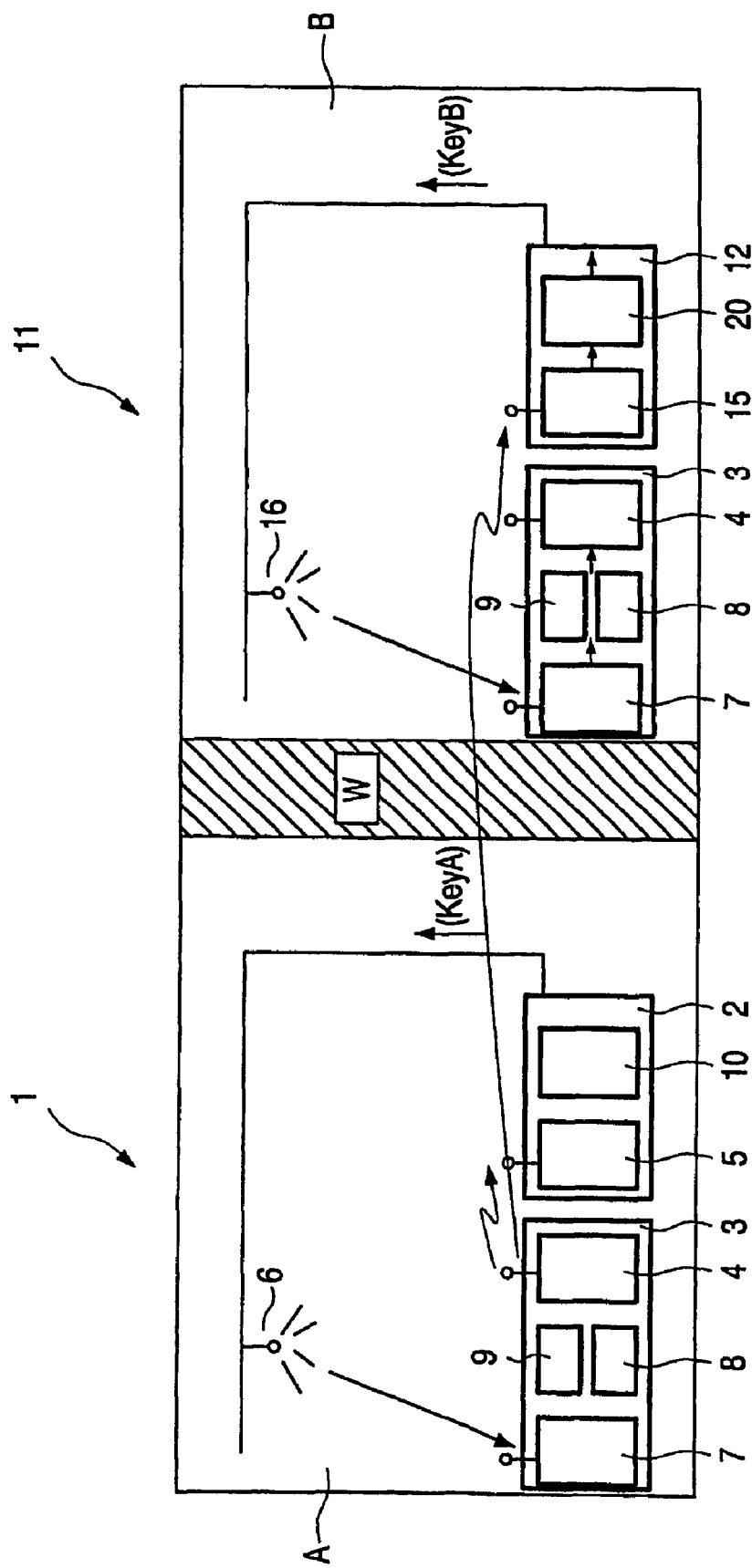
Figure 3:
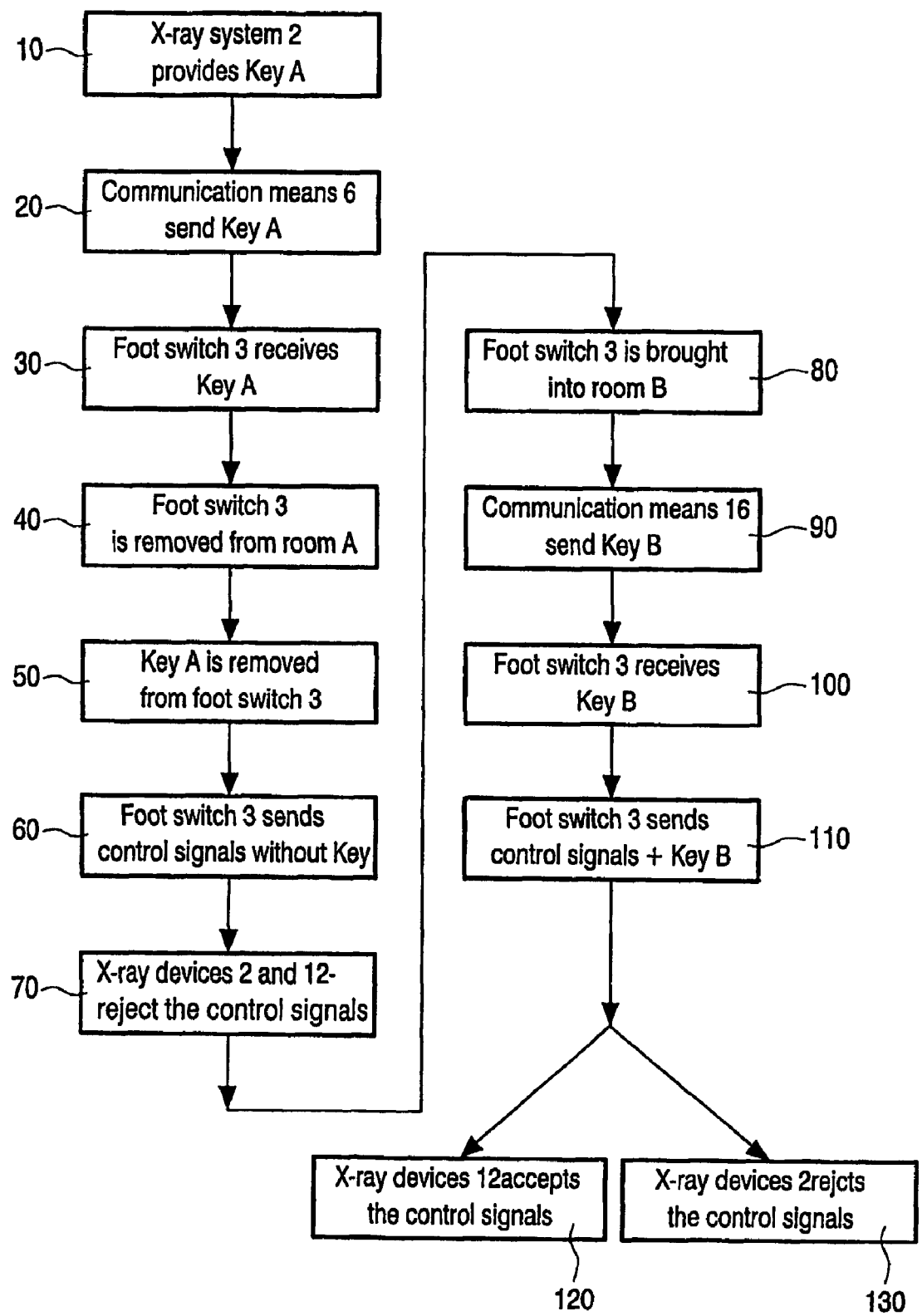
Figure 4:
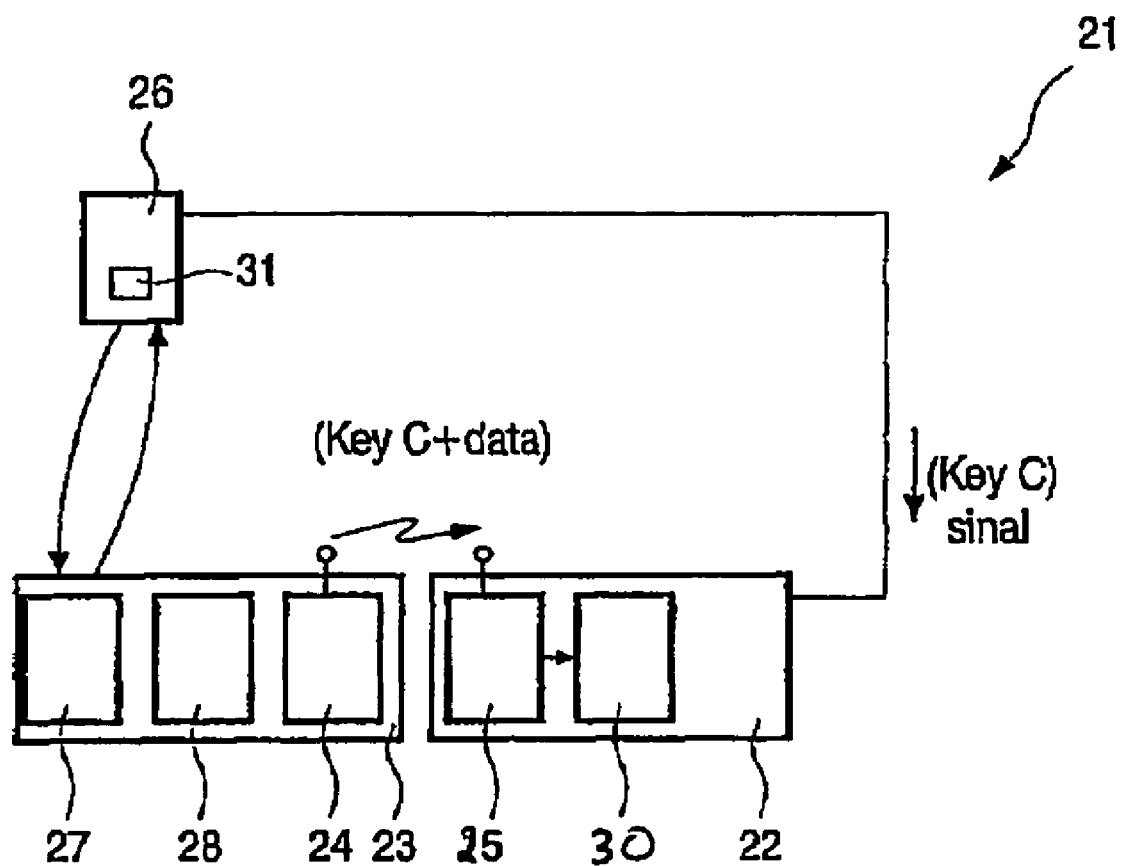

The invention will be further explained by means of the attached drawing, in which:

FIG. 1 schematically shows a first embodiment of the device according to the invention;

FIG. 2 schematically illustrates the functioning of the first embodiment;

FIG. 3 shows a block diagram illustrating the steps of a first embodiment of a method according to the invention;

FIG. 4 schematically shows a second embodiment of the device according to the invention; and In all figures equal objects are denoted with equal reference numerals.

FIG. 1 schematically shows a first embodiment of medical examination system according to the invention. Medical examination system 1 comprises a medical examination device, in this preferred embodiment an X-ray device 2, and a wireless control device 3 for remote operation of the X-ray device 2. In the example shown the wireless control device is an X-ray foot switch 3 provided with battery supply.

The foot switch 3 is provided with a radio frequent (RF) transmitter 4 to transmit signals comprising control signals accompanied by an identification code to the X-ray device 2. The X-ray device 2 is provided with a radio frequent receiver 5 to receive said signals.

The examination system 1 further comprises communication means 6 comprising Infra Red transmitter means for automatically periodically transmitting the identification code to the foot switch 3. The foot switch 3 is provided with Infra Red receiver means 7 for receiving the identification code. In the foot switch memory means 8 are present for temporal storage of the identification code. Eraser means 9 are used to erase the identification code from the memory means after a predefined period of time.

The X-ray device 2 is coupled to the transmitter means 6 to provide the identification code. Any unique code may be used as identification code. Preferably the identification code comprises a room identification code identifying the examination room A in which the X-ray device 2 is located.

The X-ray device 2 is provided with means 10 to verify the identification code and is arranged to accept the corresponding control signals when the identification code is correct and to reject the corresponding control signals when the identification code is not correct.

FIG. 2 schematically illustrates the functioning of the first embodiment of the system according to the invention. Two adjacent examination rooms A and B are shown that are separated by a wall W. The medical examination system 1 is situated in room A. In room B another examination system 11 according to the invention is located having similar components as system 1. The corresponding components of system 11 are denoted with corresponding reference numerals incremented by 10. System 11 comprises: an X-ray device 12 having an RF receiver 15 and verification means 20, and communication means 16.

System 11 uses the foot switch 3 from system 1 provided with an RF transmitter 4, Infra Red receiver means 7, memory means 8 and eraser means 9.

FIG. 3 shows a block diagram illustrating the functioning of the system according to the invention when the foot switch 3 is removed from room A and brought into room B.

In step 10 X ray system 2 in room A sends a room identification code Key A to the communication means 6.

In step 20 communication means 6 periodically send the room identification code Key A to the foot switch 3 which is present in room A. In this example one or more omni-directional Infrared senders 6 are used. As this provides multi-path connections by reflection from walls and other objects, the Key A signal will not be blocked by intervening objects. As Infra Red radiation does not penetrate the walls the signal will be confined to room A.

In step 30 the foot switch 3 receives the room identification code Key A and temporally stores it in the memory means 8.

In step 40 the foot switch 3 is removed from room A.

In step 50 the eraser means 9 erase Key A from the memory means 8. The eraser means may comprise standard data eraser means that automatically operate after a predetermined time period. As the foot switch 3 is located outside room A it can no longer receive Key A.

In step 60 foot switch 3 is accidentally activated and transmits RF control signals without a valid identification code.

In step 70 X-ray system 2 and X-ray system 12 may both receive the RF signals, but the verification means 10 respectively 20 will reject the control signals because of the invalid identification code and both the X-ray system 2 and X-ray system 12 will not respond to the control signals. The verification means 10 can for example be arranged to compare the identification code accompanying the signals from foot switch 3 to the room identification key A the X-ray system 2 has sent to the communication means 6 in step 10.

In step 80 foot switch 3 is brought into room B.

In step 90 communication means 16 periodically send the room identification code Key B to the foot switch 3. Preferably one or more omni-directional Infrared senders 16 are used to assure that the Key B signal will not be blocked by intervening objects and will be confined to room B.

In step 100 the foot switch 3 receives the room identification code Key B and temporally stores it in the memory means 8.

Step 90 is repeated after a predetermined time period. Step 100 will be performed as long as foot switch 3 is located in room B.

In step 110 the foot switch 3 is activated and transmits control signals accompanied by Key B.

In step 120 the RF receiver 15 receives the signals, the verification means 20 verify key B as the correct identification code and of X-ray system 12 acts according to the control signals.

In step 130 RF receiver 5 receives the signals, the verification means 10 verify key B as a false identification code and X-ray system 2 is not activated by the control signals.

FIG. 4 schematically shows a second embodiment of the system according to the invention. Medical examination system 21 partly corresponds to system 1. The corresponding components of system 21 are denoted with corresponding reference numerals incremented by 20. System 21 comprises: an X-ray device 22 having an RF receiver 25 and verification means 30, and a foot switch 23 having an RF transmitter 24, Radio Frequency IDentification (RFID) tag means 27 and memory means 28, and communication means 26 comprising an RFID reader 26.

In the memory means 28 of the foot switch 23 an identification code Key C is stored. The same identification code Key C is stored in the RFID tag 27. The communication means 26 are arranged as interrogation means for periodically retrieving the identification code from the foot switch 23. The interrogation means comprise an RFID reader 31 and the foot switch 23 is provided with an REID device 27. The RFID reader sends an RF pulse to which the RFID tag responds by returning an RF signal comprising the unique identification code Key C of the foot switch 23. The area in which the RFID reader is sensitive to the response of the RFID tag is typically a few square meters. The RFID reader 26 sends the RFID response signal comprising the identification code to the X ray device 22. The RFID reader 26 is hereto connected to the X ray device 22 by cable.

The verification means 30 are arranged to verify the accompanying identification code of each incoming control signal for the X ray device 22 with Key C and will thus accept only control signals originating from the control device having Key C as unique identification code that has made its presence known in the same examination room C.

It will be clear to a person skilled in the art that one or more foot switches can be added to the system in both embodiments allowing the system to be operated form various different positions.

Furthermore the medical examination system according to the invention is also suitable in a situation wherein two medical examination systems are situated in the same examination room. In both embodiments each control device will then be arranged to send control signals accompanied by a room identification code as well as a control device identification code to the corresponding examination device. The control device identification code should be unique in the context of an examination room. Said control device identification code should also be made known to the corresponding examination device. This can be performed by means of techniques known per se in the art. The verification means will be arranged to only accept the control signals when both the room identification code and the control device identification code are verified.

In the second embodiment 21 (see FIG. 4) due to the limited response area of the RFID reader 26 the room identification code sent by the RFID tag 27 naturally will reach only the RFID reader 26. In the same manner the room identification code sent by the RFID tag of a similar additional system in the same examination room naturally will reach only the RFID reader of the additional system. This will reduce the chance of errors occurring in case the communication of the control device identification code failed.

In the first embodiment 1 of the invention however, in case of failure to communicate the control device identification code, possible errors will now only occur in the same examination room under direct supervision of skilled personnel that has the possibility to intervene to prevent real danger.

Summarizing the invention refers to a medical examination device operable by a remote control device, wherein means are provided for automatic assignment of an identification code to the control device and/or the medical examination device, which code is necessary for operation of the medical examination device by the control device.

The invention is thus of course not limited to the described or shown embodiments, but generally extends to any embodiment, which falls within the scope of the appended claims as seen in light of the foregoing description and drawings.

The invention claimed is:

1. A medical examination system comprising:
   a medical examination device;
   a control device to operate the medical examination device;
   wherein the control device transmits signals comprising control signals accompanied by an identification code, comprising a room identification code identifying the room in which the examination device is located, and wherein the examination device is provided with means to verify the identification code and is arranged to accept the corresponding control signals when the identification code is correct and to reject the corresponding control signals when the identification code is not correct;
   communication means for automatically communicating the identification code between the control device and the examination device; and
   an erasing device that erases the identification code from a memory of the control device at a predetermined time independent of the location of the medical examination device and the control device.

2. The medical examination system according to claim 1, wherein the communication means are arranged to receive the identification code from the medical examination device for transmittance to the control device.

3. The medical examination system according to claim 1, wherein the communication means are arranged for periodically transmitting the identification code and the control device is provided with memory means for temporal storage of the identification code.

4. The medical examination system according to claim 1, wherein the communication means comprise Infra Red transmitter means and the control device is provided with Infra Red receiver means.

5. The medical examination system according to claim 1, wherein the communication means are arranged to receive the identification code from the control device for transmittance to the examination device.

6. The medical examination system according to claim 5, wherein the communication means comprise interrogation means for periodically retrieving the identification code from the control device.

7. The medical examination system according to claim 6, wherein the interrogation means comprise an RFID reader and the control device is provided with an RFID tag.

8. The medical examination system according to claim 1, wherein the control device is provided with a radio frequency transmitter and the examination device is provided with a radio frequency receiver.

9. The medical 1 examination system according to claim 1, wherein the examination device comprises an X-ray device.

10. The medical examination system according to claim 9, wherein the control device is an X-ray foot switch.

11. The medical examination system according to claim 1, wherein the communication means comprises a communication device that is associated with an exam room, wherein the communication device emits a signal having a strength that confines the signal to the exam room.

12. The medical examination system according to claim 1, wherein the medical examination device is immobile.

13. The medical examination system according to claim 1, wherein the communication means is immobile.

14. A method for automatically communicating an identification code between a control device and a medical examination device in a medical examination system, the method comprising the acts of:
   a) receiving the identification code from the medical examination device by a communication means, said identification code identifying the room in which the examination device is located;
   b) transmitting the identification code periodically to the control device by the communication means;
   c) temporally storing the identification code in a memory of the control device; and
   d) erasing the identification code from the memory of the control device at a predetermined time independent of the location of the medical examination device and the control device.

15. The method according to claim 14, wherein the communication means comprises a communication device that is associated with an exam room, wherein the communication device emits a signal having a strength that confines the signal to the exam room.

16. The method according to claim 14, wherein the medical examination device is immobile.

17. The method according to claim 14, wherein the communication means is immobile.

* * * * *